United States Patent [19]

Hohlweg et al.

[11] Patent Number: 5,512,562
[45] Date of Patent: Apr. 30, 1996

[54] TRICYCLIC 2,3,4,5-TETRAHYDRO-1H-3-BENZAPINES

[75] Inventors: Rolf Hohlweg, Kvistgaard; Erik B. Nielsen, Værløse, both of Denmark

[73] Assignee: Novo Nordisk A/S, Bagsvaerd, Denmark

[21] Appl. No.: 202,401

[22] Filed: Feb. 24, 1994

[30] Foreign Application Priority Data

Mar. 10, 1993 [DK] Denmark .................... 0267/93

[51] Int. Cl.⁶ .................. C07D 223/14; C07D 491/048; C07D 495/04; A01K 31/55
[52] U.S. Cl. .................. 514/215; 514/217; 540/578; 540/580; 540/586
[58] Field of Search .................... 540/586, 578, 540/580; 514/215, 217

[56] References Cited

U.S. PATENT DOCUMENTS

| | | |
|---|---|---|
| 4,255,445 | 3/1981 | Brush et al. ............... 424/285 |
| 4,751,222 | 6/1988 | Bræstrup et al. ............ 514/213 |

FOREIGN PATENT DOCUMENTS 0135767  4/1985  European Pat. Off. .

OTHER PUBLICATIONS

*Cecil Textbook of Medicine*, 19th ed (1992), Wyngaarden, M. D. editor, pp. 2075–2078.

*Primary Examiner*—Philip I. Datlow
*Attorney, Agent, or Firm*—Steven T. Zelson; Cheryl H. Agris

[57] ABSTRACT

Tricyclic benzazepines having the general formula

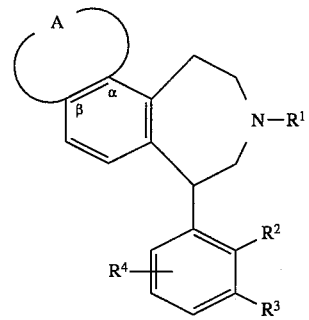

wherein A together with the α- and β-marked carbon atoms is a cyclopentene, cyclohexene, furan, dihydrofuran, pyran, dihydropyran, thiophene, oxazole, pyrrole, pyrroline, tetrahydropyridine or dioxole ring, $R^1$ is H or alkyl, $R^2$ and $R^3$ independently are H, alkoxy, halogen, nitro, cyano or hydroxy, or $R^2$ and $R^3$ together may form a furan, dihydrofuran, cyclopentene or dioxole ring and $R^4$ is H, alkoxy, nitro, cyano, hydroxy or halogen, or a pharmaceutically acceptable salt thereof, are useful in treatment of certain disorders in the central nervous system, e.g., psychosis, pain, depression, sleep disturbances, dyskinesia, Parkinson's disease, stroke.

7 Claims, No Drawings

TRICYCLIC 2,3,4,5-TETRAHYDRO-1H-3-BENZAPINES

This invention relates to novel tricyclic benzazepines and pharmaceutically acceptable acid addition salts thereof, to methods for their preparation, to pharmaceutical compositions containing them, and to their use in the treatment of certain disorders in the central nervous system, related to dysfunctions of the dopamine receptor system, e.g. psychosis, pain, depression, sleep disturbances, dyskinesia, Parkinson's disease, stroke.

In the last decade intensive pharmacological research concerning benzazepines has taken place. The pharmacological properties of benzazepines depend to a large extent on the substituents. Various substituted benzazepines exhibiting neuroleptic, anti-aggressive, anti-Parkinson and vascular effects are known.

U.S. Pat. Ser. No. 4,255,445 discloses tricyclic benzazepines having peripheral dopaminergic activity. These compounds are all 4-hydroxy-1-methyl-6-phenyl-1,6,7,8,9,10-hexahydro2H-furo[3,2-g][3]benzazepines.

It has now been found that a group of tricyclic benzazepine compounds of a different structure surprisingly exhibit strong antidopaminergic effect which makes them useful in psychopharmaceutical applications.

According to the present invention there are provided tricyclic benzazepines of the general formula I

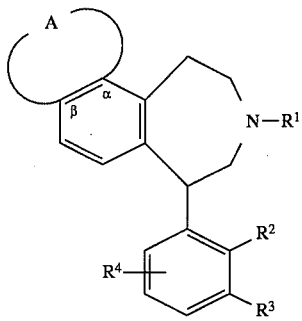

(I)

wherein A together with the α- and β-marked carbon atoms is a cyclopentene, cyclohexene, furan, dihydrofuran, pyran, dihydropyran, thiophene, oxazole, pyrrole, pyrroline, tetrahydropyridine or dioxole ring, $R^1$ is hydrogen or $C_{1-6}$-alkyl, $R^2$ and $R^3$ independently are hydrogen, $C_{1-6}$-alkoxy, halogen, nitro, cyano or hydroxy, or $R^2$ and $R^3$ together may form a furan, dihydrofuran, cyclopentene or dioxole ring, $R^4$ is hydrogen, $C_{1-6}$-alkoxy, nitro, cyano, hydroxy, or halogen or a pharmaceutically acceptable salt thereof.

Specific compounds of formula (I) are:
6-(benzofuran-7-yl)-8-methyl-7,8,9,10-tetrahydro-6H-furo[2,3-g][3]benzazepine,
6-(2,3-dihydrobenzofuran-7-yl)-8-methyl-2,3,7,8,9,10-hexahydro-6H-furo[2,3g][ 3]benzazepine,
5-(benzofuran-7-yl)-3-methyl- 1,2,3,4,5,8,9,10-octahydroindeno [4,5-d]azepine,
6-(benzofuran-7-yl)-8-methyl-7,8,9,10-tetrahydro-6H-thieno[2,3-g][3]benzazepine,
1-(2,3-dihydrobenzofuran-7-yl)-6,7-methylenedioxy-3-methyl-2,3,4,5-tetrahydro-1H- 3-benzazepine,
3-Methyl-5-phenyl- 1,2,3,4,5,8,9,10,-octahydroindeno [4,5-d]azepine,
3-Methyl-5-phenyl-2,3,4,5,8,9,10,11 -octahydro-1H-naphth [1,2-d]azepine,
8-Methyl-6-phenyl-7,8,9,10-tetrahydro-6H-oxazolo[4,5-g][3]benzazepine.

The compounds of formula I may be presented as a mixture of enantiomers, which may be resolved into the individual pure enantiomers. This resolution may conveniently be performed by fractional crystallization, from various solvents of the salts of compounds of the formula I with optical active acids or by other methods known from the literature, e.g. chiral column chromatography. Therefore, this invention includes all isomers, whether resolved or mixtures thereof.

Particularly valuable embodiments of this invention are non-toxic, pharmaceutically acceptable acid addition salts of benzazepines of formula I. Such salts include those derived from inorganic and organic acids such as hydrochloric, hydrobromic, sulphuric, phosphoric, methanesulfonic, acetic, lactic, maleic, phthalic and tartaric acids.

These salts may be prepared by methods known to professionals skilled in the art.

The invention further provides pharmaceutical compositions comprising the compounds of the invention. The dosage formulation will preferably contain the active compounds in the range of 0.1 mg to about 1000 mg for oral dosing. Typical dosage for antipsychotic effect would vary between about 0.5 to 10 mg/kg per day divided in 2 or 3 doses, administered orally.

This invention also relates to methods of preparing the above mentioned compounds. These methods comprise:

a) reacting a 2-arylethylamine of formula IV

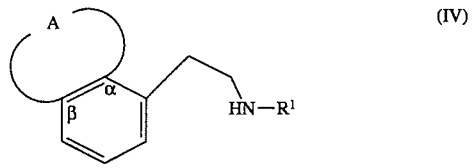

(IV)

wherein $R^1$ is hydrogen or lower alkyl and A is defined as above, with an oxirane of the general formula III

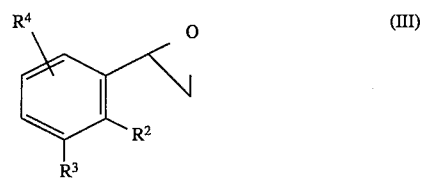

(III)

wherein $R^2, R^3$ and $R^4$ are defined as above and by heating at a temperature between 50° C. and 110° C., to form a compound of formula II

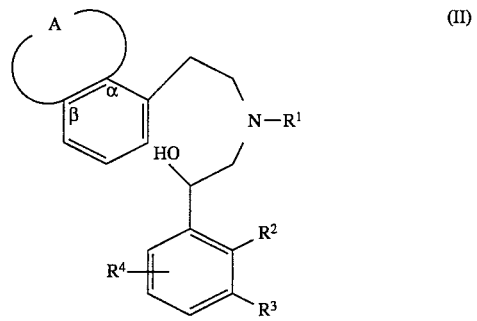

(II)

wherein A, $R^1$, $R^2$, $R^3$ and $R^4$ are as defined above and transferring a compound of formula II into the desired benzazepines of formula I:

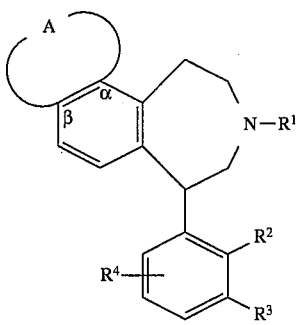

by means of an intramolecular cyclization effected by reacting the aminoalcohols of formula II with reagents such as trifluoroacetic acid, sulfuric acid, methanesulfonic acid, polyphosphoric acid or mixtures thereof or other acidic or dehydrating media, or b) reacting a 2-arylethylamine of formula V

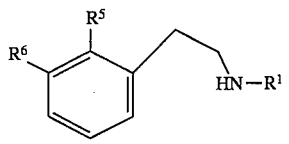

wherein $R^1$ is hydrogen or lower alkyl and $R^5$ and $R^6$ independently are hydroxy, mercapto, amino, carboxy, or $R^5$ and $R^6$ independently represent substituents, which can be transformed to hydroxy, mercapto, amino or carboxy groups by standard procedures known to a person skilled in the art, with an oxirane of the general formula III

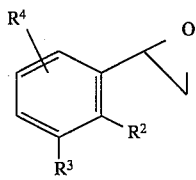

wherein $R^2$, $R^3$ and $R^4$ are defined as above and by heating at a temperature between 50° C. and 110° C., to form a compound of formula VI

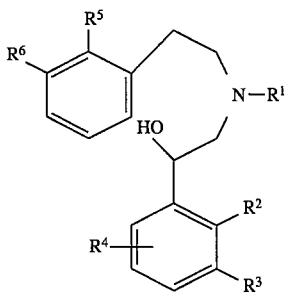

wherein $R^1$, $R^2$, $R^3$, $R^4$, $R^5$ and $R^6$ are as defined above and transferring a compound of formula VI into the benzazepines of formula VII:

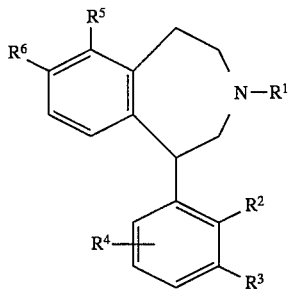

by means of an intramolecular cyclization effected by reacting the aminoalcohols of formula VI with reagents such as trifluoroacetic acid, sulfuric acid, methanesulfonic acid, polyphosphoric acid or mixtures thereof or other acidic or dehydrating media.

Preferably the cyclization is performed in a mixture of sulfuric acid (1–20%) and trifluoroacetic acid at temperatures between −10° C. and +20° C.

Transferring benzazepines of formula VII to the desired condensed benzazepines of formula I in a cycloaddition reaction leading to a group A as defined above.

The cycloaddition may for example be carried out by reacting a benzazepine of formula VII, wherein $R^5$ and $R^6$ are hydroxyl, with a dihalomethane and a base in a solvent such as DMF, leading to a benzazepine of formula I, where A is a methylenedioxy group.

The starting materials employed in the syntheses of the compounds of formula I are known to a person skilled in the art.

For example may a compound of formula IV

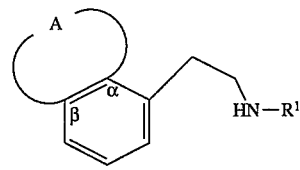

wherein A is defined as above be synthesized by standard procedures in several steps known to experts skilled in the art, for example starting with the corresponding arylaldehyde.

The compounds of the invention are useful because of their pharmacological activity. In particular, the compounds of the invention are active in assays predictive for antipsychotic effect. Thus the compounds of formula I were tested for their binding to dopamine $D_1$ receptor in homogenates from rat striatum using the method described (Life Science vol. 37, p. 1971 (1985) P. Andersen et al.) and the result appears from Table I. $IC_{50}$ is the affinity of tested compounds for the dopamine $D_1$ receptor.

TABLE I

| Test Compound | $IC_{50}$ (nM) Dopamine $D_1$ receptor |
|---|---|
| Example 1 | 12 |

The compound of the invention, together with a conventional adjuvant, carrier, or diluent, and if desired in the form of a pharmaceutically acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form or sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing 0.1–1000 mg of active ingredient or, more specified 0.5–10 mg, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, syrup, peanut oil, olive oil, gelatin, lactose, terra alba, sucrose, agar, pectin, acacia, amylose, magnesium stearate, talc, silicic acid, stearic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or colouring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compounds of the invention are dispensed in unit dosage form comprising 0.05–100 mg in a pharmaceutically acceptable carrier per unit dosage.

A typical tablet, which may be prepared by conventional tabletting techniques, contains:

| | |
|---|---|
| Active compound | 1.0 mg |
| Lactosum | 67.8 mg Ph. Eur. |
| Avicel ® | 31.4 mg |
| Amberlite ® IRP 88 | 1.0 mg |
| *Magnesii stearas* | 0.25 mg Ph. Eur. |

The following examples illustrate the preparation of the novel compounds of this invention:

EXAMPLE 1

6-(Benzofuran-7-yl)-8-methyl-7,8,9,10-tetrahydro-6H-furo[2,3-g][3]benzazepine

A. 7-Carboxymethylbenzofuran was prepared by known methods from 7-chloromethylbenzofuran via the nitrile and subsequent hydrolysis and obtained as a white crystalline powder. M.p. 115–118° C.

$^1$H-NMR in CDCl$_3$ [δ, ppm]:3.98 (s,2H); 6.78 (d,1H); 7.20 (m, 2H); 7.55 (dd, 1H); 7.65 (d, 1H).

B. Benzofuran-7-yl-N-methylacetamide

To a solution of 9.9 g (0.056 mol) 7-carboxymethylbenzofuran in 50 ml toluene 6.1 ml (0.084 mol) thionylchloride was added. The mixture was refluxed until the evolution of gas ceased (45 min). Solvents were removed in vacuo and the residue was stripped with toluene. The crude acid chloride was dissolved in 80 ml acetone and was slowly added to a vigorously stirred ice cold 40% aqueous methylamine solution. The resulting yellow solution was concentrated in vacuo until crystallization started. The product was filtered off, washed with water and dried. Yield: 9.06 g (85%) of the compound as an offwhite powder. M.p. 138–142° C.

$^1$H-NMR in CDCl$_3$ [δ, ppm]: 2.75 (d, 3H); 3.85 (s, 2H); 5.6 (broad s, 1H); 6.8 (d, 1H); 7.25 (m, 2H); 7.55 (dd, 1H); 7.67 (d, 1H).

C. 2-(Benzofuran-7-yl)ethyl-N-methylamine 8.70 g benzofuran-7-yl-N-methylacetamide and 5.21 g (0.138 mol) sodiumborohydride were dissolved in 100 ml dioxane. Acetic acid was added dropwise to the chilled solution. Then, the reaction mixture was warmed slowly and refluxed for 1 h. After cooling to room temperature, 25 ml 6N HCl was added and the mixture was warmed to reflux for 5 min. The mixture was cooled, pH adjusted to 10 and the mixture was extracted with dichloromethane. The organic layer was washed with water and brine, dried over sodium sulfate and concentrated in vacuo. The remaining oil was distilled (B.p. 111–114° C/1 mm Hg). The compound was obtained as colourless oil, 3.7 g (46%).

$^1$H-NMR in CDCl$_3$ [δ, ppm]1.17 (broad s, 1H); 2.45 (s, 3H); 3.05 (m, 4H); 6.77 (d, 1H); 7.15 (m, 2H); 7.45 (dd, 1H); 7,63 d, 1H).

D. 2-[[2-(Benzofuran-7-yl)ethyl]methylamino]-1-(benzofuran-7-yl)ethanol 1.0 g (0.0057 mol) 2-(benzofuran-7-yl)ethyl-N-methylamine and 1.39 g (0.0085 mol) 7-epoxyethylbenzofuran were dissolved in 5 ml acetonitrile and refluxed for 24 h. The solvent was evaporated in vacuo and the remanence was redissolved in toluene. The solution was extracted with 150 ml 1N HCl. The aqueous solution was adjusted to alkaline pH and extracted with toluene. The organic phase was washed with water and brine, dried over sodium sulfate and concentrated in vacuo. The title compound was obtained as a yellowish syrup. Yield: 1.87 g (97%).

$^1$H-NMR in CDCl$_3$ [δ, ppm]: 2.50 (s, 3H); 2.65–3.25 (m, 6H); 3.95 (broad s, 1H); 5.23 (dd, 1H); 6.77 (d, 1H); 6.78 (d, 1H); 7.05–7.30 (m, 3H); 7.47–7.55 (m, 3H); 7.62 (d, 1H); 7.63 (d, 1H).

E. 6-(Benzofuran-7-yl)-8-methyl-7,8,9,10-tetrahydro-6H-furo[2,3-g][3]benzazepine 1.70 g (0.005 mol) 2-[[2-(benzofuran-7-yl)ethyl]methylamino]-1-(benzofuran7-ethanol was dissolved in 50 ml trifluoroacetic acid and cooled to 10° C. 0.3 ml conc. sulphuric acid was added to the vigorously stirred solution and the reaction mixture was kept at ambient temperature for 90 min. The solution was concentrated in vacuo to 20 ml and poured onto a mixture of 50 ml 4N sodium hydroxide and ice. Subsequent extraction with toluene, washing of the toluene solution with water and concentration gave the crude product as an oil, which was purified by column chromatography over silica with dichloromethane/methanol/pyridine 96:4:1 as the eluent. The pure product was obtained as an amorphous powder. This was dissolved in ether and precipitated as the hydrochloride by adding a solution of HCl in ether giving 480 mg (27%) of a white crystalline powder. M.p. 259–261° C.

$^1$H-NMR in CDCl$_3$ [δ, ppm]: 2,85 (d, 3H); 3.00 (m, 1H); 3.65–4.10 (m, 5H); 5.59 (d, 1H); 6.35 (d, 1H); 6.74 (d, 1H); 6.85 (d, 1H); 7.20–7.35 (m, 3H); 7.53–7.70 (m, 3H); 13.40 (broad s, 1H).

EXAMPLE 2

6-(2,3-Dihydrobenzofuran-7-yl)-8-methyl-2,3,7,8,9,10-hexahydro-6H-furo[2,3g][3]benzazepine 0.40 g (0.0011 mol) 6-(benzofuran-7-yl)-8-methyl-7,8,9,10-tetrahydro-6H-furo[2,3-g][3]benzazepine was dissolved in 30 ml ethanol, 0.12 g palladium catalyst (10% on charcoal) was added, and hydrogenation was performed in a flask connected to a gas burette with a slight excess pressure. After 16 h, a NMR-spectrum of a sample showed full conversion to the title compound. The catalyst was filtered off and the solution was concentrated in vacuo. The residue was redissolved in dichloromethane and the solution washed subsequently with 1N NaOH, water and brine. Concentration in vacuo gave a pale yellow syrup. This was redissolved in acetonitrile and the hydrochloride was precipitated by dropwise addition of conc. HCl. (Light yellow crystals. M.p. 280–283° C.).

$^1$H-NMR of the free base in CDCl$_3$ [δ, ppm]: 2.30 (dd, 1H); 2.38 (s, 3H); 2.80–3.30 (m, 9H); 4.40–4.60 (m, 5H); 6.22 (d, 1H); 6.75–6.92 (m, 3H); 7.10 (d, 1H).

EXAMPLE 3

5-(Benzofuran-7-yl)-3-methyl-1,2,3,4,5,8,9,10-octahydroindeno[4,5-d]azepine

A. 2-(Indan-4-yl)ethyl-N-methylamine

The amine was synthesized in analogy to 2-(benzofuran-7-yl)ethyl-N-methylamine (example 1C).

$^1$H-NMR in CDCl$_3$ [δ, ppm]: 2.08 (quint, 2H); 2.33 (s, 3H); 2.55–2.85 (m, 4H); 2.90 (m, 4H); 6.90–7.20 (m, 3H).

B. 2-[[2-(Indan-4-yl)ethyl]methylamino]-1-(benzofuran-7-yl)ethanol was synthesized in analogy to example 1D.

$^1$H-NMR in CDCl$_3$ [δ, ppm]: 2.08 (quint, 2H); 2.50 (s, 3H); 2.60–3.00 (m, 10H); 4.02 (broad s, 1H); 5.25 (dd, 1H); 6.77 (d, 1H); 6.90–7.30 (m, 4H); 7.47 (d, 1H); 7.52 (dd, 1H); 7.62 (d, 1H).

C. 5-(Benzofuran-7-yl)-3-methyl-1,2,3,4,5,8,9,10-octahydroindeno[4,5d]azepine was synthesized in analogy to example 1 E, from 2-{[2-(indan-4yl)ethyl]methylamino}-1-(benzufuran-7-yl) ethanol. Isolated as hydrochloride: white crystalline powder. M.p. 146–148° C.

$^1$H-NMR of free base in CDCl$_3$ [δ, ppm]: 2.07 (quint, 2H); 2.38 (s, 3H); 2.8–3.25 (m, 10H); 4.85 (dd, 1H); 6.35 (d, 1H); 6.77 (d, 1H); 6.85 (d, 1H); 7.06 (d, 1H); 7.22 (t, 1H); 7.52 (d, 1H); 7.55 (d, 1H).

EXAMPLE 4

6-(Benzofuran-7-yl)-8-methyl-7,8,9,10-tetrahydro-6H-thieno[2,3-g][3]benzazepine

A. 2-(Benzo[b]thiophen-7-yl)ethyl-N-methylamine was synthesized in analogy to example 1C.

$^1$H-NMR in CDCl$_3$ [δppm]: 1.40 (broad s, 1H); 2.40 (s, 3H); 3.02 (m, 4H); 7.15 (d, 1H), 7.30 (m, 3H); 7.67 (d, 1H).

B. 2-[[2-(Benzo[b]thiophen-7-yl)ethyl]methylamino]-1-(benzofuran-7yl)ethanol was synthesized in analogy to example 1D.

$^1$H-NMR in CDCl$_3$ [δ, ppm]: 2.55 (s, 3H); 2.65–3.2 (m, 6H); 5.24 (dd, 1H); 6.75 (d, 1H); 7.1–7.75 (m, 9H).

C. 6-(Benzofuran-7-yl)-8-methyl-7,8,9,10-tetrahydro-6H-thieno[2,3-g][3]benzazepine was synthesized in analogy to example 1 E, from 2-[[2(benzo[b]thiophen-7yl)ethyl]methylamino] 1-(benzofuran-7-yl)ethanol and isolated as the hydrochloride: white crystals. M.p. 178–184° C.

$^1$H-NMR in d$_6$-DMSO [δ, ppm]: 2.87 (d, 3H); 3.20–4.10 (m, 6H); 5.40 (d, 1H); 6.33 (d, 1H); 7.06 (d, 1H); 7.27 (d, 1H); 7.39 (t, 1H); 7.43 (d, 1H); 7.55 (d, 1H); 7.74 (d, 1H); 7.80 (d, 1H), 7.98 (d, 1H); 11.4 (broad s, 1H).

EXAMPLE 5

1-(2,3-Dihydrobenzofuran-7-yl)-6,7-methylenedioxy-3-methyl-2,3,4,5-tetrahydro-1H- 3-benzazepine A. 2,3-DimethoxyphenethyI-N-methylamine was synthesized in analogy to the previously described phenethylamines.

$^1$H-NMR in CDCl$_3$ [δ, ppm]: 1.15 (broad s, 1H); 2.45 (s, 3H); 2.83 (s, 4H); 3.83 (s, 3H); 3.87 (s, 3H); 6.80 (m, 2H); 7.0 (dd, 1H).

B. 2-[[2-(2,3-Dimethoxyphenyl)ethyl]methylamino]-1-(benzofuran-7-yl)-ethanol was synthesized in analogy to the previously described 2aminoethanols.

$^1$H-NMR in CDCl$_3$ [δ, ppm]: 2.48 (s, 3H); 2.65–2.90 (m, 6H); 3.85 (s, 6H); 5.24 (dd, 1H); 6.72–6.85 (m, 3H); 7.00 (t, 1H); 7.25 (m, 1H); 7.40–7.55 (m, 2H); 7.60 (d, 1H).

C. 1-(Benzofuran-7-yl)-6,7-dimethoxy-3-methyl-2,3,4,5-tetrahydro-1H-3benzazepine was synthesized from 2-[[2-(2,3-dimethoxyphenyl)ethyl]methylamino]-1-(benzofuran-7-yl)-ethanol, in analogy to example 1E. Colourless oil. (M.p. of the hydrochloride: 135° C).

$^1$H-NMR in CDCl$_3$ [δ, ppm]: 2.35 (m, 1H); 2.40 (s, 3H); 2.95–3.30 (m, 4H); 3.47 (dd, 1H); 3.78 (s, 3H); 3.82 (s, 3H); 4.84 (d, 1H); 6.26 (d, 1H); 6.52 (d, 1H); 6.75 (d, 1H); 7.08 (d, 1H); 7.24 (t, 1H); 7.54 (d, 1H); 7.56 (d, 1H).

D. 1-(Benzofuran-7-yl)-6,7-dihydroxy-3-methyl-2,3,4,5-tetrahydro-1H-3benzazepine 1.10 g (0.0033 mol) 1-(benzofuran-7-yl)-6,7-dimethoxy-3-methyl-2,3,4,5-tetrahydro-1-H- 3-benzazepine was dissolved in 25 ml dry dichloromethane. The solution was cooled to −60° C. and 0.93 (0.0098 mol) boron tribromide was slowly added. The reaction mixture was stirred at −60° C. for 15 min., allowed to warm up to 0° C. and stirred for 1 h. Evaporation in vacuo left a brown residue, which was redissolved in dichloromethane. The solution was stirred in an ice bath and 5 ml methanol was added dropwise. The solution was again concentrated in vacuo, the residue was dissolved in 6N HCl and refluxed for 30 min. Then pH was adjusted to 8 with 2N NaOH-solution and the product extracted with ethylacetate. The organic layer was washed with water and brine and concentrated in vacuo. 1-(Benzofuran-7-yl)-6,7-dihydroxy-3-methyl-2,3,4,5,-tetrahydro-1H-3-benzazepine was obtained as an offwhite powder.

$^1$H-NMR in CDCl$_3$ [δ, ppm]: 2.05 (m, 1H); 2.08 (s, 3H); 2.55–2.90 (m, 4H); 3.10 (dd, 1H); 4.45 (t, 1H); 5.57 (d, 1H); 6.14 (d, 1H); 6.48 (d, 1H); 6.74 (d, 1H); 6.90 (t, 1H); 7.22 (d, 1H); 7.30 (d, 1H).

E. 1-(2,3-Dihydrobenzofuran-7-yl)-6,7-dihydroxy-3-methyl-2,3,4,5-tertrahydro-1H- 3-benzazepine 0.5 g (0.0016 mol) 1-(benzofuran-7-yl)-6,7-dihydroxy-3-methyl-2,3,4,5-tetrahydro-1H-3-benzazepine was dissolved in a mixture of 25 ml ethanol and 2 ml acetic acid. 0.2 g catalyst (10% Pd/C) was added and the mixture was submitted to hydrogenation in a Parr apparatus at a pressure of 50 psi. After 24 h the catalyst was filtered off and the solution was concentrated in vacuo. The residue was redissolved in dichloromethane, the solution was washed subsequently with NaHCO3-solution, water and brine. Evaporation in vacuo gave 1-(2,3-dihydrobenzofuran-7-yl)-6,7-dihydroxy-3-methyl-2,3,4,5-tetrahydro-1H-3-benzazepine as an offwhite foam.

$^1$H-NMR in CDCl$_3$ [δ, ppm]: 2.38 (s and m, 4H); 2.80–3.42 (m, 7H); 4.45 (t and m, 3H); 6.00 (d, 1H); 6.40 (d, 1H); 6.80 (m, 2H); 7.09 (m, 1H).

F. 1-(2,3-Dihydrobenzofuran-7-yl)-6,7-methylenedioxy-3-methyl-2,3,4,5-tetrahydro-1H-3-benzazepine 0.27 g (0.00087 mol) 1-(2,3-dihydrobenzofuran-7-yl)-6,7-dihydroxy-3-methyl-2,3,4,5-tetrahydro-1 H-3-benzazepine was dissolved in 1 ml DMF. 0.66 g cesium fluoride was added and the mixture was stirred at room temperature for 1 h. Then 0.1 ml dichloromethane was added and the mixture was heated in a screw cap vial to 110° C. for 1 h. After cooling, the mixture was extracted with ether. The ether solution was washed with water, dried over anhydrous sodium sulfate and concentrated in vacuo. The crude product was purified by preparative TLC. 1-(2,3-dihydrobenzofuran-7-yl)-6,7-methylenedioxy-3-methyl-2,3,4,5-tetrahydro-1H-3benzazepine was obtained as the hydrochloride from ether by treating the solution with gaseous HCl. (White crystalline powder).

$^1$H-NMR in CDCl$_3$ [δ, ppm]: 2.84 (d, 3H); 2.93 (dd, 1H); 3.10–3.90 (m, 7H); 4.53 (t, 2H); 4.98 (d, 1H); 5.95 (s, 2H); 6.08 (d, 1H); 6.53 (d, 1H); 6.87 (t, 1H); 7.00 (d, 1H); 7.20 (d, 1H).

EXAMPLE 6

3-Methyl-5-phenyl-1,2,3,4,5,8,9,10,-octahydroindeno[4,5-d]azepine

A. 2-[[2-(Indan-4-yl)ethyl]methylamino]-1-phenylethanol was synthesized in analogy to example 1D from 2-(indan-4-yl)ethyl-N-methylamine and phenyloxirane.

$^1$H-NMR in CDCl$_3$ [δ, ppm]: 2.00–2.15 (m, 2H); 2.92 (t, 4H); 3.02 (s, 3H); 3.11–3.36 (m, 6H); 5.37 (d, 1H); 6.97–7.17 (m, 3H); 7.28–7.39 (m, 5H).

B. 3-Methyl-5-phenyl-1,2,3,4,5,8,9,10-octahydroindeno[4,5-d]azepine was synthesized in analogy to example 1E. Isolated as hydrochloride: white crystals. M.p. 238–240° C.

$^1$H-NMR in CDCl$_3$ [δ, ppm]: 2.02–2.16 (m, 2H); 2.76–3.00 (m, 8H); 3.11–3.33 (m, 2H); 5.08 (d, 1H); 6.35 (d, 1H); 6.92 (d, 1H); 7.19–7.45 (m, 5H); 13.27 (broad s, 1H).

EXAMPLE 7

3-Methyl-5-phenyl-2,3,4,5,8,9,10,11-octahydro-1H-naphth[1,2-d]azepine

A. 2-(1,2,3,4-Tetrahydronaphth-5-yl)ethyl-N-methylamine

The amine was synthesized after known methods, e.g. as shown in example 1 and isolated as the hydrochloride.

$^1$H-NMR in d$_6$-DMSO [δ, ppm]: 1.67–1.75 (m, 4H); 2.48–2.78 (m, 7H); 2.86–3.05 (m, 4H); 6.93–7.09 (m, 3H); 9.19 (broad s, 2H).

B. 2-[[2-(1,2,3,4-Tetrahydronaphth-5-yl)ethyl]methylamino]-1-phenylethanol was synthesized from 7A and phenyloxirane in analogy to example 1D.

$^1$H-NMR in CDCl$_3$ [δ, ppm]: 1.73–1.86 (m, 4H); 2.45 (s, 3H); 2.51–2.81 (m, 11H); 3.98 (broad s, 1H); 4.68 (t, 1H); 6.90–7.06 (m, 3H); 7.23–7.36 (m, 5H).

C. 3-Methyl-5-phenyl-2,3,4,5,8,9,10,11-octahydro-1H-naphth[1,2-d]azepine was synthesized from 7B in analogy to example 1E. The compound was isolated as the hydrochloride. White crystals. M.p. 247°–250° C.

$^1$H-NMR in d$_6$-DMSO [δ, ppm]: 1.67–1.76 (m, 4H); 2.65–2.78 (m, 7H); 3.29–3.78 (m, 6H); 4.87 (d, 1H); 6.13 (d, 1H); 6.78 (d, 1H); 7.18–7.48 (m, 5H); 11.63 (broad s, 1H).

EXAMPLE 8

8-Methyl-6-phenyl-7,8,9,10-tetrahydro-6H-oxazolo[4,5-g][3]benzazepine

A. 2-(3-Methoxy-2-nitrophenyl)ethylamine was synthesized after standard methods from 3-methoxy-2-nitrobenzaldehyde. The compound was isolated as the hydrochloride. Colorless crystals. M.p. 200°–203° C.

$^1$H-NMR of the free base in CDCl$_3$ [δ, ppm]: 1.55 (broad s, 2H); 2.70 (t, 2H); 2.98 (t, 2H); 3.90 (s, 3H); 6.88 (d, 2H); 7.36 (t, 1H).

B. 2-[2-(3-Methoxy-2-nitrophenyl)ethylamino]-1-phenylethanol was synthesized in analogy to example 1D from 2-(3-methoxy-2-nitrophenyl)-ethylamine and phenyloxirane. White crystalline powder. M.p. 99°–101° C.

$^1$H-NMR in CDCl$_3$ [δ, ppm]: 1.50 (broad s, 1H); 2.65–2.80 (m, 3H); 2.85–2.98 (m, 3H); 3.50 (broad s, 1H); 3.89 (s, 3H); 4.67 (dd, 1H); 6.87 (d, 1H); 6.90 (d, 1H); 7.23–7.40 (m, 6H).

C. 7-Methoxy-6-nitro-1-phenyl-2,3,4,5-tetrahydro-1H-3-benzazepine 2.25 g (0.0071 mol) 2-[2-(3-Methoxy-2-nitrophenyl)ethylamino]-1-phenylethanol were suspended in 20 ml n-heptane. 17.5 g polyphosphoric acid was added and the vigorously stirred mixture was heated to reflux for 2 hours. 100 ml water were added and the cooled mixture was neutralized with 4n NaOH. The heptane was separated and the aqueous phase was extracted with dichloromethane. The combined organic phases were washed with water and saturated brine. Evaporation yielded the crude product which was purified by column chromatography on silica with n-heptane/THF 1:2 as eluent. The pure compound was obtained as a light yellow syrup.

$^1$H-NMR in CDCl$_3$ [δ, ppm]: 1.95 (broad s, 1H); 2.70–2.78 (m, 2H); 2.93–3.03 (m, 2H); 3.33 (dd, 1H); 3.50 (dd, 1H); 3.84 (s, 3H); 4.29 (dd, 1H); 6.73 (d, 1H); 6.89 (d, 1H); 7.13 (d, 2H); 7.22–7.42 (m, 3H).

D. 7-Methoxy-3-methyl-6-nitro-1-phenyl-2,3,4,5-tetrahydro-1H-3-benzazepine 0.40 g (0.00134 mol) 7-methoxy-6-nitro-1-phenyl-2,3,4,5-tetrahydro-1H-3-benzazepine was dissolved in a mixture of 5 ml formic acid and 4 ml 35% aqueous formaldehyde. The mixture was heated to reflux for 2.5 hours and then evaporated in vacuo. The residue was partitioned between dichloromethane and saturated NaHCO3-solution, the organic layer was washed twice with water and once with brine, dried with NaSO$_4$ and concentrated in vacuo, yielding the compound as a light yellow oil.

$^1$H-NMR in CDCl$_3$ [δ, ppm]: 2.39 (s, 3H); 2.30–2.45 (m, 1H); 2.67–3.15 (m, 5H); 3.82 (s, 3H); 4.34 (d, 1H); 6.68 (s, 2H); 7.13–7.43 (m, 5H).

E. 7-Hydroxy-3-methyl-6-nitro-1-phenyl-2,3,4,5-tetrahydro-1H-3-benzazepine 0.40 g (0.00128 mol) 7-methoxy-3-methyl-6-nitro-1-phenyl-2,3,4,5-tetrahydro1H-3-benzazepine was dissolved in 6 ml dry dichloromethane. The solution was cooled to –20° C. and 1.5 ml boron tribromide was added dropwise. The reaction mixture was stirred at –20° C. for 15 min and at room temperature for 2.5 h. Then, the mixture was concentrated in vacuo and the residue was hydrolized by careful addition of methanol. 10 ml water was added and the solution was heated to reflux for 0.5h. The cooled solution was adjusted to pH 8.5 by addition of NaHCO$_3$-solution and extracted with dichloromethane. Evaporation of the solvent yielded the compound as a yellow powder.

$^1$H-NMR in CDCl$_3$ [δ, ppm]: 2.43 (s, 3H); 2.52 (dd, 1H); 2.75–3.25 (m, 5H); 4.39 (dd, 1H); 6.56 (s, 2H); 7.05–7.40 (m, 6H).

F. 6-Amino-7-hydroxy-3-methyl-1-phenyl-2,3,4,5-tetrahydro-1H-3-benzazepine 0.16 g (0.00053 mol) 7-hydroxy-3-methyl-6-nitro-1-phenyl-2,3,4,5-tetrahydro-1H-3-benzazepine was dissolved in 15 ml ethanol. 0.05 g 10%Pd/C-catalyst were added and hydrogenation was carried out at a burette apparatus for 2h. The catalyst was filtered off and the solution was concentrated in vacuo. The compound was obtained as a light brown powder.

$^1$ H-NMR in CDCl$_3$ [δ, ppm]: 2.95 (s, 3H); 3.05–3.40 (m, 6H); 3.20 (broad s, 2H); 4.58 (d, 1H); 6.52 (d, 1H); 7.15–7.45 (m, 7H).

G. 8-Methyl-6-phenyl-7,8,9,10-tetrahydro-6H-oxazolo[4,5-g][3]benzazepine 0.12 g (0.00043 mol) 6-amino-7-hydroxy-3-methyl-1-phenyl-2,3,4,5-tetrahydro1H- 3-benzazepine and 0.80 g 1,3,5-triazine were dissolved in 12 ml toluene and heated to reflux for 16h. TLC indicated complete reaction and formation of a single product. The reaction mixture was concentrated in vacuo and stripped several times with toluene. The compound was obtained as a light brown foam.

$^1$H-NMR in CDCl$_3$ [δ, ppm]: 2.43 (s, 3H); 2.53 (m, 1H); 2.42 (m, 1H); 3.00–3.15 (m, 2H); 3.37 (ddd, 1H); 3.55 (ddd, 1H); 6.75 (d, 1H); 7.15–7.40 (m, 6H); 8.06 (s, 1H).

We claim:

1. Tricyclic 2,3,4,5-tetrahydro-1H-3-benzazepines of the formula I wherein A together with the α- and β-marked carbon atoms is a cyclopentene, cyclohexene, furan, dihydrofuran, pyran, dihydropyran, thiophene, oxaxole, pyrrole, pyrroline, tetrahydropyridine or dioxole ring, $R^1$ is hydrogen or $C_{1-6}$-alkyl, $R^2$ and $R^3$ independently are hydrogen, $C_{1-6}$-alkoxy, halogen, nitro, cyano or hydroxy, or $R^2$ and $R^3$ together may form a furan, dihydrofuran, cyclopentene or dioxole ring, $R^4$ is hydrogen, $C_{1-6}$-alkoxy, nitro, cyano, hydroxy, or halogen or a pharmaceutically acceptable salt thereof.

2. The compound according to claim 1 wherein $R^1$ is methyl.

3. A compound according to claim 1 which is
6-(benzofuran-7-yl)-8-methyl-7,8,9,10-tetrahydro-6H-furo [2,3-g][3]benzazepine,
6-(2,3-dihydrobenzofuran-7-yl)-8-methyl-2,3,7,8,9,10-hexahydro-6H-furo[2,3-g][3]benzazepine,
5-(benzofuran-7yl)-3-methyl-1,2,3,4,5,8,9,10-octahydroindeno [4,5-d]azepine,
6-(benzofuran-7-yl)-8-methyl-7,8,9,10-tetrahydro-6H-thieno[2,3-g][3]benzazepine,
1-(2,3-dihydrobenzofuran-7-yl)-6,7-methylenedioxy-3-methyl-2,3,4,5-tetrahydro-1H- 3-benzazepine,
3-Methyl-5-phenyl-1,2,3,4,5,8,9,10-octahydroindeno [4,5-d]azepine,
3-Methyl-5-phenyl-2,3,4,5,8,9,10,11-octahydro-1H-naphth [1,2-d]azepine,
8-Methyl-6-phenyl-7,8,9,10-tetrahydro-6H-oxazolo [4,5-g ][3]benzazepine.

4. A pharmaceutical composition comprising a compound according to claim 1 or a pharmaceutically acceptable acid addition salt thereof and a pharmaceutically acceptable carrier or diluent.

5. A pharmaceutical composition according to claim 4 wherein it is in the form of an oral dosage unit containing 0.1–100 mg of the active compound.

6. A method of treating a central nervous system ailment related to dysfunction of Dopamine D1 receptor in a person in need of such treatment characterized in administering to said person an amount of a compound according to claim 1 effective in alleviation of such an ailment.

7. A method of treating a central nervous system ailment related to a dysfunction of Dopamine D1 receptor in a person in need of such treatment characterized in administering to said person an amount of a compound according to claim 1 which is effective for the alleviation of such ailment in the form of a pharmaceutical composition thereof, in which it is present together with a pharmaceutically acceptable carrier or diluent.

* * * * *